United States Patent [19]

Lange et al.

[11] Patent Number: 4,508,734

[45] Date of Patent: Apr. 2, 1985

[54] SUBSTITUTED N-BENZOYL-N-PHENOXYPHENYLUREAS, THE MANUFACTURE, AND THE USE THEREOF FOR COMBATING INSECTS

[75] Inventors: Arno Lange, Mannheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 278,667

[22] Filed: Jun. 29, 1981

[51] Int. Cl.[3] .................... A01N 47/34; C07C 127/22

[52] U.S. Cl. .................................... 514/594; 564/44

[58] Field of Search ........................ 564/44; 424/322

[56] References Cited

U.S. PATENT DOCUMENTS 3,992,553 11/1976 Sirrenberg et al. .................. 564/44
4,005,223 1/1977 Sirrenberg et al. .................. 564/44
4,041,177 8/1977 Sirrenberg et al. .................. 564/44

FOREIGN PATENT DOCUMENTS 55-38357 3/1980 Japan .
1492364 11/1977 United Kingdom .

OTHER PUBLICATIONS

Wellinga et al., J. Agr. Food Chem., vol. 21, No. 3, (1973), pp. 348-354.

*Primary Examiner*—Nicky Chan
*Attorney, Agent, or Firm*—Keil & Weinkauf

[57] ABSTRACT

N-benzoyl-N'-phenoxyphenylureas of the formula

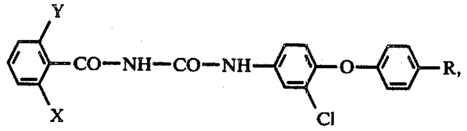

(I)

where X, Y and R have the meanings given in the disclosure.

The compounds are suitable as adulticides and ovicides for combating insects.

5 Claims, No Drawings

SUBSTITUTED N-BENZOYL-N-PHENOXYPHENYLUREAS, THE MANUFACTURE, AND THE USE THEREOF FOR COMBATING INSECTS

The present invention relates to substituted N-benzoyl-N'-phenoxyphenylureas, a process for their manufacture, and insecticides containing these compounds as active ingredients.

The use of N-benzoyl-N'-phenoxyphenylureas as insecticides has already been disclosed (J. Agr. Food Chem., 21, 348, 1973, DE-A 2,531,202).

We have now found that substituted N-benzoyl-N'-phenoxyphenylureas of the formula

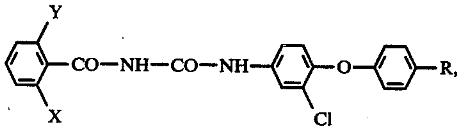
(I)

where X and Y denote fluorine or chlorine and R denotes fluorine, chlorine or bromine, have a better insecticidal action than prior art N-benzoyl-N'-phenoxyphenylureas.

Compounds of the formula I in which X is fluorine are preferred.

The novel compounds may be prepared by reaction of (a) a compound of the formula

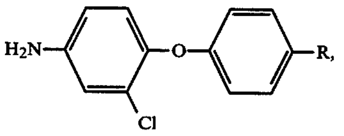
(II)

where R has the above meanings, with a benzoyl isocyanate of the formula

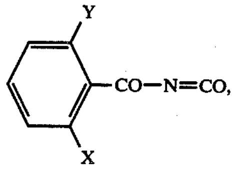
(III)

where X and Y have the above meanings, or (b) a compound of the formula

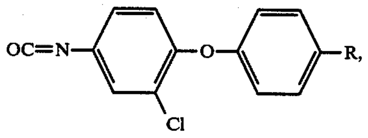
(IV)

where R has the above meanings, with a benzamide of the formula

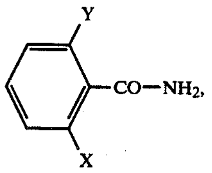
(V)

where X and Y have the above meanings.

Processes (a) and (b) are preferably carried out in solvents or diluents, such as hydrocarbons and chlorohydrocarbons, e.g., benzene, toluene, xylene, gasoline, methylene chloride, chloroform, carbon tetrachloride, and chlorobenzene, in ethers, e.g., diethyl ether, dibutyl ether and dioxane, in ketones, e.g., acetone, methyl ethyl ketone, methyl isopropyl ketone, and methyl isobutyl ketone, or in nitriles, e.g., acetonitrile or benzonitrile.

As a rule, the reaction takes place at atmospheric pressure and from 0° to 120° C., and preferably from 20° to 50° C. The reactants are advantageously employed in equimolar amounts. It is not necessary for the starting materials to be pure.

The following examples illustrate the invention:

EXAMPLE 1

At room temperature, 6.4 g of 3-chloro-4-(4-chlorophenoxy)aniline is dissolved in 50 ml of toluene. Subsequently, 4.7 g of 2,6-difluorobenzoyl isocyanate is dripped in, whereupon the temperature rises by 15° C. The mixture is then stirred for 1 hour at 50° C. and allowed to cool; the precipitate is then filtered off. There is obtained 8.5 g of N-(2,6-difluorobenzoyl)-N'-[4-(4-chlorophenoxy)-3-chlorophenyl]-urea of m.p. 194°-196° C.

The following compounds are prepared analogously:

2. N-(2,6-difluorobenzoyl)-N'-[4-(4-fluorophenoxy)-3-chlorophenyl]-urea, m.p.: 159°-161° C.
3. N-(2,6-difluorobenzoyl)-N'-[4-(4-bromophenoxy)-3-chlorophenyl]-urea, m.p.: 182°-186° C.
4. N-(2,6-dichlorobenzoyl)-N'-[4-bromophenoxy)-3-chlorophenyl]urea, m.p.: 208°-210° C.
5. N-(2,6-dichlorobenzoyl)-N'-[4-(4-chlorophenoxy)-3-chlorophenyl]-urea, m.p.: 186°-189° C.
6. N-(2,6-dichlorobenzoyl)-N'-[4-(4-fluorophenoxy)-3-chlorophenyl]-urea, m.p.: 183°-185° C.
7. N-(2-chloro-6-fluorobenzoyl)-N'-[4-(4-chlorophenoxy)-3-chlorophenyl]-urea, m.p.: 173°-175° C.
8. N-(2-chloro-6-fluorobenzoyl)-N'-[4-(4-fluorophenoxy)-3-chlorophenyl]-urea, m.p.: 179°-183° C.
9. N-(2-chloro-6-fluorobenzoyl)-N'-[4-(4-bromophenoxy)-3-chlorophenyl]-urea, m.p.: 179°-181° C.

The compounds of the formula I according to the invention are suitable for effectively combating insects. They are suitable as adulticides and ovicides.

Examples of injurious insects from the Lepidoptera order are *Plutella maculipennis, Leucoptera coffeella, Hyponomeuta malinellus, Argyresthia conjugella, Sitotroga cereallella, Phthorimea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus pinia-*

*rus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar. Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectorialis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sercata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus macroccanus, Schistocerca peregrina, Nomadacris septemfasciata, Melanoplus spretus, Melanoplus femurrubrum, Blatta orientalis, Blattella germanica, Periplaneta americana,* and *Blabera gigantea.*

The compounds according to the invention may be successfully employed as pesticides for crop protection, and in the hygiene, stores protection and veterinary sectors. They may be employed as contact and stomach poisons.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 3 parts by weight of compound no. 1 is intimately mixed with 97 parts by weight of particulate kaolin. A dust is obtained containing 3% by weight of the active ingredient.

II. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of compound no. 5 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dedecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

The amount of active ingredient applied in the open may vary from 0.2 to 10 kg/ha, and is preferably from 0.5 to 2.0 kg/ha.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiopene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethylphosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, 1 -biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[-2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N- acetylphosphoramidothioate, α-hexachlorocyclohexane, 1,1-di-(p-methoxyphenyl)-2,2,2-trichloroethane, b 2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methylcyclopenten-(2)-on-(1)-yl-(4)-DL-cis,trans-chrysanthemate, 5-benzylfuryl-(3)-methyl-DL-cis,trans-chrysanthemate, 3-phenoxybenzyl(+)-cis,trans-2,2-dimethyl-3-(2,2-dichlorovinyl)-cyclopropancarboxylate, α-cyano-3-phenoxybenzyl(+)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The following examples demonstrate the biological action of the new compounds. The active ingredients used for comparison purposes are N-(2-methylbenzoyl)-N'-[4-(4-chlorophenoxy)-3-chlorophenyl]-urea (I) and N-(2-fluorobenzoyl)-N'-[4-(4-chlorophenoxy)-3-chlorophenyl]-urea (II) disclosed in German DE-A No. 2,531,202.

EXAMPLE A

Breeding experiment with mosquito larvae (*Aedes aegypti*)

The active ingredient formulations are added to 200 ml of tapwater; 30 to 40 Aedes larvae in the 4th stage are then introduced.

The temperature is kept at 25° C. Pupation and hatching of the imagoes are assessed against an untreated control.

Feeding is carried out once during the experiment with a conventional powdered fish good.

In this test, active ingredients 1 to 9 exhibit a better action than comparative agents I and II.

EXAMPLE B

Breeding experiment with houseflies (*Musca domestica*)

50 g of a culture medium consisting of 100 parts of water, 10 parts of baker's yeast, 10 parts of dried milk, and 1 part of agar is thoroughly mixed, while warm, with aqueous formulations of the active ingredients. After the culture medium has cooled, approx. 0.1 ml of flies' eggs are placed on it and their development observed for one week. The temperature is kept at 20° C.

EXAMPLE C

Breeding experiment with cotton stainers (*Dysdercus intermedius*)

50 g of cottonseed is swollen for 24 hours in aqueous solutions of the active ingredients. The supernatant liquid is then poured off, and 20 stainers in the penultimate stage are placed in 1 liter jars, the bottoms of which are covered with moist sand. For 7 days, these animals are fed exclusively on the pretreated cottonseed. Subsequently, untreated food is then offered.

EXAMPLE D

Breeding experiment with Tribolium castaneum 10 g samples of wheat flour are carefully mixed with the active ingredient formulations, and the mixtures are introduced into 250 ml glass bottles. 20 beetles are then placed in each bottle for egg-laying. The beetles are sieved off after 14 days. The treated flour with the laid eggs is kept at 24° C. and observed until the next beetle generation hatches.

In Examples B, C and D, the new compounds, especially active ingredients nos. 1 and 5, have a much better action than comparative agent I.

We claim:

1. A substituted N-benzoyl-N'-phenoxyphenylurea of the formula

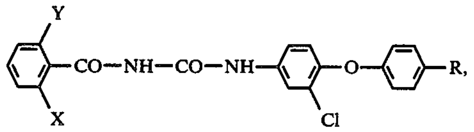

(I)

where X and Y denote fluorine or chlorine and R denotes fluorine, chlorine or bromine.

2. N-(2,6-difluorobenzoyl)-N'-[4-(4-chlorophenoxy)-3-chlorophenyl]-urea.

3. N-(2,6-dichlorobenzoyl)-N'-[4-(4-chlorophenoxy)-3-chlorophenyl]-urea.

4. An insecticidal agent comprising inert additives and an effective amount of an N-benzoyl-N'-phenoxyphenylurea of the formula I as set forth in claim 1.

5. A process for combating insects which comprises: allowing an insecticidally effective amount of an N-benzoyl-N'-phenoxyphenylurea of the formula I as set forth in claim 1 to act on the insects, their eggs and/or their habitat.

* * * * *

UNITED STATES PATENT AND TRADEMARK OFFICE
CERTIFICATE OF CORRECTION

PATENT NO. : 4,508,734

DATED : April 2, 1985

INVENTOR(S) : Arno LANGE et al.

It is certified that error appears in the above-identified patent and that said Letters Patent is hereby corrected as shown below:

On the Title Page insert

--[30] Foreign Application Priority Data

July 16,1980 [DE] Fed. Rep. of Germany 3026825 --.

Signed and Sealed this

*Twenty-second* Day of *July 1986*

[SEAL]

*Attest:*

DONALD J. QUIGG

*Attesting Officer* *Commissioner of Patents and Trademarks*